(12) United States Patent
Kubo

(10) Patent No.: US 10,143,365 B2
(45) Date of Patent: Dec. 4, 2018

(54) LIGHT SOURCE UNIT FOR ENDOSCOPE AND ENDOSCOPY SYSTEM

(71) Applicant: FUJIFILM Corporation, Tokyo (JP)

(72) Inventor: Masahiro Kubo, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 114 days.

(21) Appl. No.: 15/096,643

(22) Filed: Apr. 12, 2016

(65) Prior Publication Data

US 2016/0296107 A1 Oct. 13, 2016

(30) Foreign Application Priority Data

Apr. 13, 2015 (JP) .................................. 2015-081718

(51) Int. Cl.
*A61B 1/06* (2006.01)
*A61B 1/00* (2006.01)
(Continued)

(52) U.S. Cl.
CPC ........ *A61B 1/0653* (2013.01); *A61B 1/00009* (2013.01); *A61B 1/043* (2013.01);
(Continued)

(58) Field of Classification Search
CPC ... A61B 1/0652; A61B 1/00009; A61B 1/043; A61B 1/0646; A61B 1/0684;
(Continued)

(56) References Cited

U.S. PATENT DOCUMENTS

| 7,510,699 B2 * | 3/2009 | Black ................... A61B 5/0071 424/426 |
| 2009/0118579 A1 * | 5/2009 | Duerschinger ...... A61K 9/4808 600/109 |

(Continued)

FOREIGN PATENT DOCUMENTS

| JP | 2010-131265 A | 6/2010 |
| JP | 2011-041758 A | 3/2011 |

(Continued)

OTHER PUBLICATIONS

Extended European Search Report, dated Jul. 28, 2016, for European Application No. 16161619.8.

(Continued)

*Primary Examiner* — John P Leubecker
*Assistant Examiner* — William Chou
(74) *Attorney, Agent, or Firm* — Birch, Stewart, Kolasch & Birch, LLP

(57) ABSTRACT

Provided are a light source unit for an endoscope and an endoscopy system, which clarify the color difference between a first dye and a second dye in an observation image. The light source unit has a white LED light source and a band limiting section. The white LED light source has an excitation light source that emits blue excitation light and a phosphor layer that emits yellow fluorescence upon receipt of the excitation light. As a mixture of the fluorescence and part of the excitation light, the white LED light source outputs light having an intensity spectrum continuous across blue, green and red regions. The band limiting section reduces part of the output light in a wavelength band of not lower than a threshold. The threshold is not less than 650 nm. At the threshold, the first dye (pyoktanin) has an optical reflectance of not less than a constant value, whereas the (Continued)

second dye (indigocarmine) has an optical reflectance of substantially zero.

7 Claims, 6 Drawing Sheets

(51) Int. Cl.
| | |
|---|---|
| A61B 1/04 | (2006.01) |
| A61K 49/00 | (2006.01) |
| A61M 31/00 | (2006.01) |
| F21V 9/08 | (2018.01) |
| H04N 5/225 | (2006.01) |
| F21V 9/30 | (2018.01) |
| A61B 90/30 | (2016.01) |
| F21Y 101/00 | (2016.01) |

(52) U.S. Cl.
CPC .......... *A61B 1/0646* (2013.01); *A61B 1/0684* (2013.01); *A61K 49/006* (2013.01); *A61K 49/0021* (2013.01); *A61K 49/0023* (2013.01); *A61M 31/005* (2013.01); *F21V 9/08* (2013.01); *F21V 9/30* (2018.02); *H04N 5/2256* (2013.01); *A61B 2090/309* (2016.02); *F21Y 2101/00* (2013.01); *H04N 2005/2255* (2013.01)

(58) Field of Classification Search
CPC ............. A61K 49/0021; A61K 49/006; A61M 31/005; F21V 9/08; F21V 9/16; H04N 5/2256
USPC ....... 600/108, 109, 160, 178, 179, 180, 181, 600/182
See application file for complete search history.

(56) References Cited

U.S. PATENT DOCUMENTS

| | | | |
|---|---|---|---|
| 2009/0306478 A1* | 12/2009 | Mizuyoshi | ........... A61B 1/0638 600/178 |
| 2012/0264120 A1* | 10/2012 | Toyota | ............. G01N 33/57419 435/6.11 |
| 2013/0120678 A1* | 5/2013 | Chao | ........................ G02F 1/01 349/34 |
| 2013/0120688 A1 | 5/2013 | Chao et al. | |
| 2013/0120980 A1 | 5/2013 | Eichenholz | |
| 2014/0121468 A1 | 5/2014 | Eichenholz | |
| 2015/0009310 A1 | 1/2015 | Morimoto et al. | |
| 2015/0238086 A1* | 8/2015 | Saito | ................... A61B 5/0075 600/339 |

FOREIGN PATENT DOCUMENTS

| | | |
|---|---|---|
| JP | 2013-105746 A | 5/2013 |
| JP | 5654167 B1 | 1/2015 |

OTHER PUBLICATIONS

Japanese Office Action, dated May 30, 2018, for Japanese Application No. 2015-081718, as well as an English machine translation.

* cited by examiner

LIGHT SOURCE UNIT FOR ENDOSCOPE AND ENDOSCOPY SYSTEM

CROSS-REFERENCE TO RELATED APPLICATIONS

This application claims priority under 35 U.S.C § 119(a) to Japanese Patent Application No. 2015-081718 filed on Apr. 13, 2015. The above application is hereby expressly incorporated by reference, in its entirety, into the present application.

BACKGROUND OF THE INVENTION

1. Field of the Invention

The present invention relates to a light source unit for endoscopes and an endoscopy system.

2. Description Related to the Prior Art

In the medical field, endoscopy systems, which are each equipped with an endoscope, a light source unit for the endoscope and a processor unit, are widely used for diagnoses. The light source unit emits illumination light, which travels through a light guide inside the endoscope and is projected from a tip portion of the endoscope toward an observation object. The tip portion of the endoscope has an imaging device integrated therein so that light returned from the observation object is received on the imaging device. The processor unit processes image signals acquired by the imaging device, to produce an observation image.

As the light source unit, ones emitting white broadband light (white light) from a discharge-type light source device, such as xenon lamp, have been popular. In recent years, semiconductor illuminants, such as light emitting diodes (LED), are being adopted in place of the discharge-type light source device.

Known as a light source unit using semiconductor illuminants is a light source employing an additive method, hereinafter referred to as an additive light source, which produces white light by adding up light from red LEDs, light from green LEDs and light from blue LEDs (refer to United States Patent Application Publication No. 2015/0009310 (corresponding to Japanese Patent No. 5654167), for example). Also a white LED light source that produces white light by exciting phosphors is known as a light source unit using semiconductor illuminants (refer to JPA No. 2011-41758, for example).

Some endoscopy system may perform dye-spraying on the observation object according to the diagnostic purpose so that the imaging device will image the observation object stained with a dye or dyes (refer to JPA No. 2010-131265, for example). Pyoktanin and indigocarmine may be cited as typical dyes therefor. Pyoktanin is also called crystal violet.

Pyoktanin is a violet dye and mainly used for large intestines as observation objects. By spraying pyoktanin onto the observation object, a lesion therein is stained violet, clarifying the superficial architecture of the lesion. By the pattern of the architecture, the symptomatic state of the lesion (whether the lesion is benign or malignant) can be determined.

Indigocarmine is a blue dye and used for a wide range of observation objects, including stomachs and small and large intestines. By spraying indigocarmine onto the observation object, the superficial profile of the observation object is made clear, increasing the visibility of the lesion.

However, when observing the observation object scattered with pyoktanin, indigocarmine or another dye through an endoscopy system, the color of the dye in the observed image will change depending on the intensity spectrum of illumination light which is projected from the light source unit of the endoscopy system toward the observation object. In particular, the colors of dyes observed on an endoscopy system equipped with a light source unit having a discharge-type light source device may differ from the colors of the same dyes observed on an endoscopy system equipped with a light source unit having a semiconductor illuminant.

As shown in FIG. 6, the optical reflectance of pyoktanin (a first dye) is above a certain level in a wavelength band of not higher than approximately 470 nm and in a wavelength band of not lower than approximately 640 nm. Thus, pyoktanin is observed in violet because blue reflection light having the wavelength band of not higher than approximately 470 nm and red reflection light having the wavelength band of not lower than approximately 640 nm are received on the imaging device.

Meanwhile, the optical reflectance of indigocarmine (a second dye) is above a certain level in a wavelength band of not higher than approximately 520 nm and in a wavelength band of not lower than approximately 670 nm. Thus, indigocarmine is observed in blue because light of the wavelength band of not higher than approximately 520 nm is mainly received on the imaging device.

Therefore, depending on the degree of content of red band wavelength components of not lower than approximately 640 nm in the illumination light that is projected to the observation object, the observed colors of pyoktanin and indigocarmine will change. For example, when the illumination light contains less red band wavelength components, both pyoktanin and indigocarmine will be observed in blue, making it difficult to discriminate therebetween. On the contrary, when the wavelength components of the illumination light range from the red band to the infrared region, both pyoktanin and indigocarmine will be observed in violet, making it difficult to discriminate therebetween.

SUMMARY OF THE INVENTION

The present invention addresses an object to provide a light source unit for endoscopes and an endoscopy system, which enable clarifying the difference in color between a first dye and a second dye in an observation image.

To achieve the above object, a light source unit for an endoscope in accordance with the present invention comprises a semiconductor illuminant and a band limiting section. The semiconductor illuminant has an excitation light source that generates excitation light and a phosphor layer that is caused by the excitation light to generate fluorescence, the semiconductor illuminant emitting output light that has an intensity spectrum across blue, green and red regions. The band limiting section reduces the light intensity of the output light in a wavelength band equal to and higher than a threshold which is not less than 650 nm. At the threshold, a first dye has an optical reflectance of not less than a constant value and a second dye has an optical reflectance of substantially zero, the second dye having different optical reflection characteristics from the first dye.

Preferably, the intensity spectrum of the output light is continuous across the blue, green and red regions, and the output light includes wavelength components of not lower than 700 nm.

The first dye is preferably pyoktanin, and the second dye is preferably indigocarmine.

Preferably, the excitation light is blue light having a center wavelength of 450 nm, and the fluorescence is yellow light.

The output light is preferably a mixture of the fluorescence and those components of the excitation light which travel through the phosphor layer. The semiconductor illuminant is preferably a white light emitting diode.

An endoscopy system in accordance with the present invention comprises a semiconductor illuminant, a band limiting section, an illuminating section, an imaging device and an observation image producer. The semiconductor illuminant has an excitation light source that generates excitation light and a phosphor layer that is caused by the excitation light to generate fluorescence, the semiconductor illuminant emitting output light that has an intensity spectrum across blue, green and red regions. The band limiting section reduces the light intensity of the output light in a wavelength band equal to and higher than a threshold which is not less than 650 nm. At the threshold, a first dye has an optical reflectance of not less than a constant value and a second dye has an optical reflectance of substantially zero, the second dye having different optical reflection characteristics from the first dye. The illuminating section projects illumination light as light transmitted through the band limiting section toward the observation object. The imaging device captures light returned from the observation object and outputs color image signals. The observation image producer produces an observation image by processing the color image signals.

Preferably, the endoscopy system further includes a dye spraying section for spraying the first dye or the second dye to the observation object. The first dye is preferably pyoktanin, and the second dye is preferably indigocarmine.

According to the present invention, the band limiting section reduces the light intensity of the output light from the semiconductor illuminant in the wavelength band of not lower than the threshold that is not less than 650 nm, at which threshold the optical reflectance of the first dye is not less than a constant value and the optical reflectance of the second dye having different optical reflection characteristics from the first dye is substantially zero. Therefore, the present invention makes it possible to clarify the color difference between the first dye and the second dye in the observation image.

BRIEF DESCRIPTION OF THE DRAWINGS

The above and other objects and advantages of the present invention will be more apparent from the following detailed description of the preferred embodiments when read in connection with the accompanying drawings, wherein.

DESCRIPTION OF THE PREFERRED EMBODIMENTS

Figure 1:
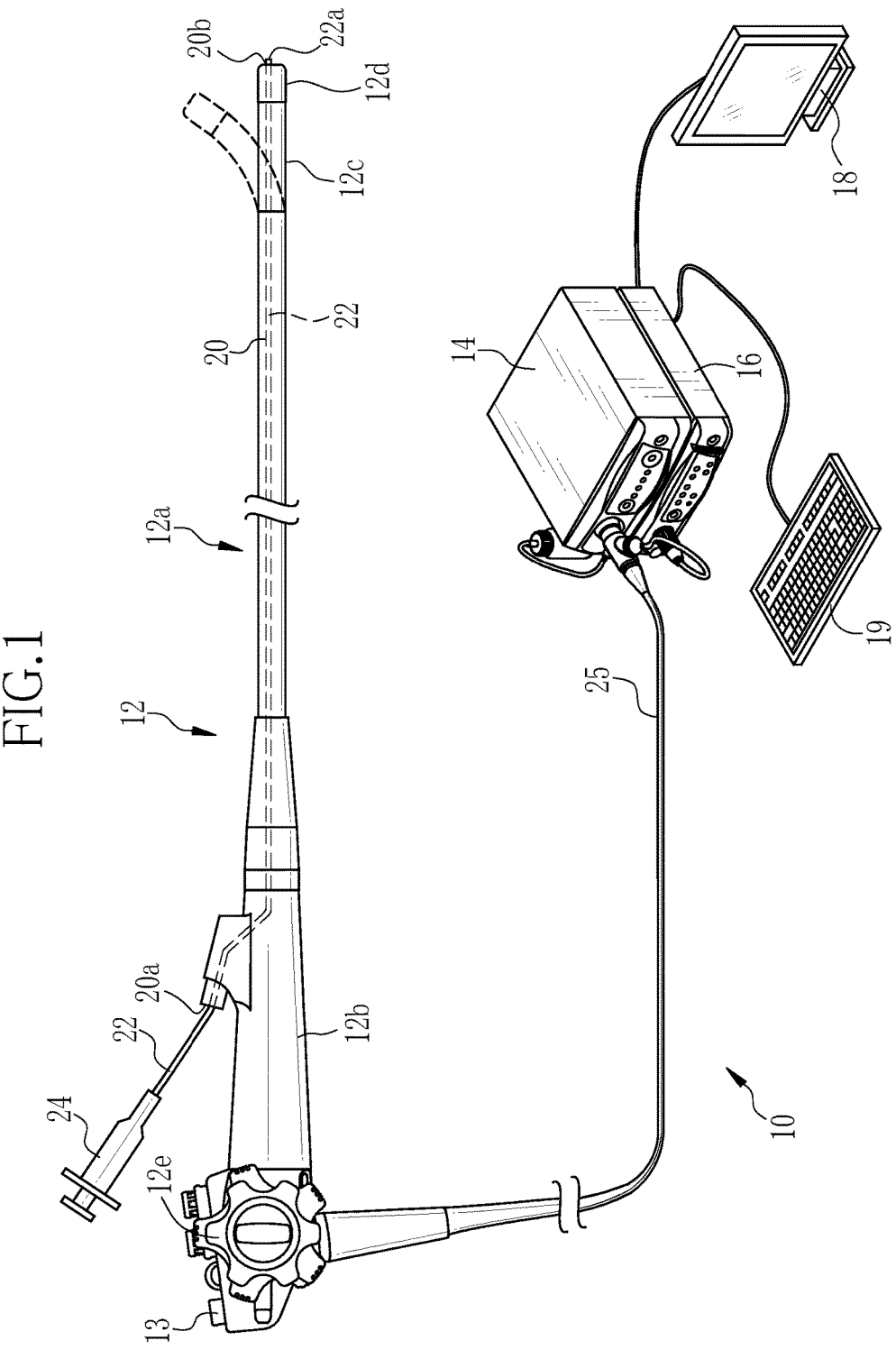
FIG. 1 is a schematic diagram illustrating an outer appearance of an endoscopy system.

In FIG. 1, an endoscopy system 10 has an endoscope 12, a light source unit for the endoscope 14, a processor unit 16, a monitor 18 and a console 19. A universal cord 25 connects the endoscope 12 optically to the light source unit 14 and electrically to the processor unit 16.

The endoscope 12 has an insertion section 12a is to be inserted in a test body, a control section 12b provided on a proximal end of the insertion section 12a, a bending section 12c provided on a distal end of the insertion section 12a, and a tip portion 12d provided at a distal end of the bending section 12c. Operating an angle-adjusting knob 12e of the control section 12b bends the bending section 12c, thereby directing the tip portion 12d to a desired orientation. The control section 12b is further provided with other members than the angle-adjusting knob 12e, such as a zooming section 13.

The processor unit 16 is electrically connected to the monitor 18 and the console 19. The monitor 18 is a display unit for displaying output image information and others. The console 19 functions as a user interface that accepts input operations such as function-settings. Note that the processor unit 16 is capable of being connected to an external recording section (not shown) for recording the image information and the like.

The endoscope 12 is also provided with an instrument channel 20. A spray tube 22 for spraying dyes onto an observation object may be inserted through the instrument channel 20. The spray tube 22 is inserted from an instrument entrance 20a, which is provided at the control section 12b, into the instrument channel 20. The spray tube 22 is exposed at least at a distal end 22a thereof from an instrument exit 20b that is formed through the tip portion 12d of the endoscope 12.

To a proximal end of the spray tube 22, an injection syringe 24 filled with pyoktanin (a first dye) or indigocarmine (a second dye) is connected. A user, such as doctor, operates the injection syringe 24 so as to spray the dye from the distal end 22a of the spray tube 22 toward the observation object. Note that the "dye spraying section" in the present invention corresponds to a feature including the spray tube 22 and the injection syringe 24.

Figure 2:
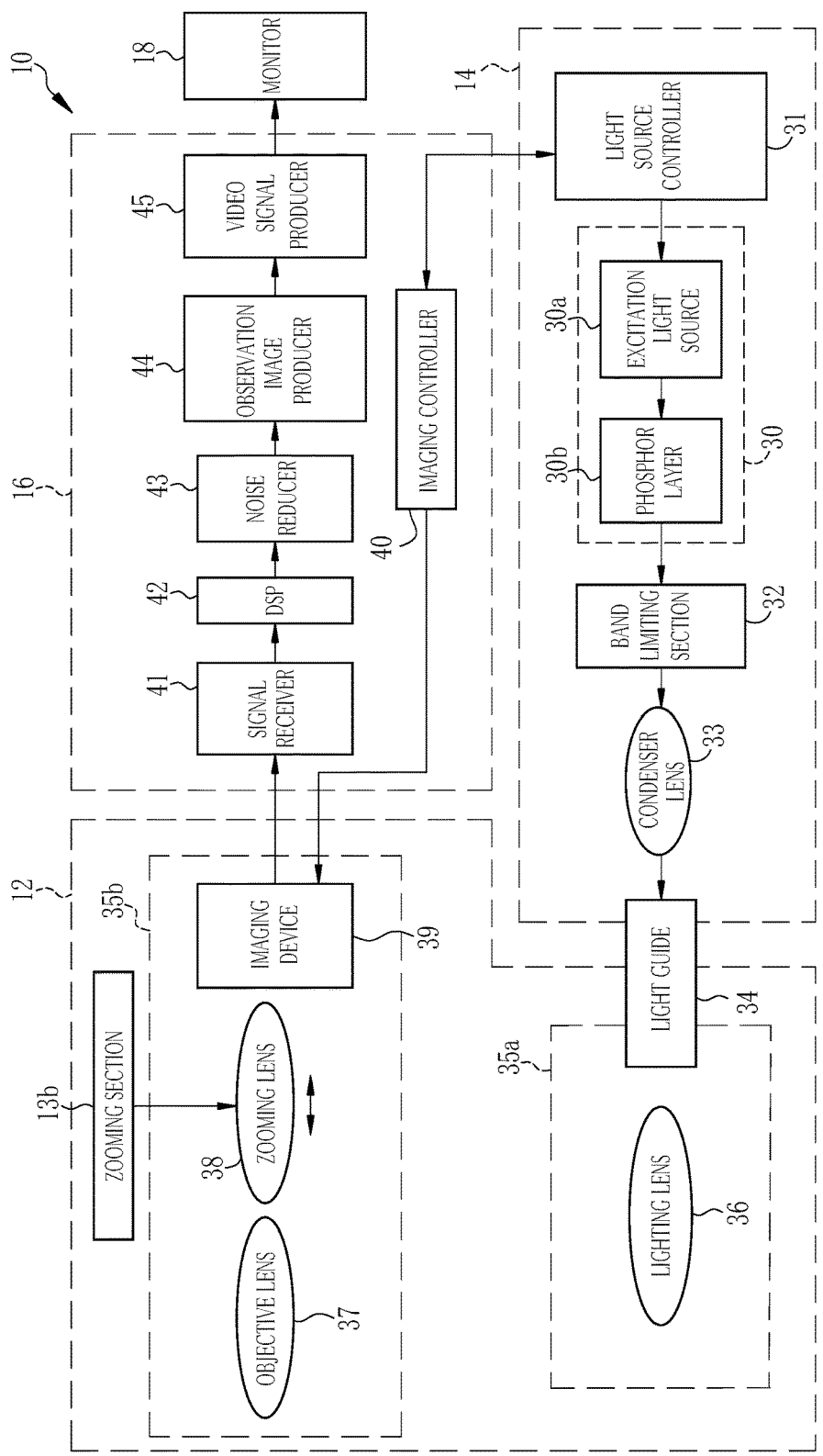
FIG. 2 is a block diagram illustrating the functions of the endoscopy system.

In FIG. 2, the light source unit 14 has a white LED light source 30, a light source controller 31 and a band limiting section 32. The white LED light source 30 is a semiconductor illuminant constituted of an excitation light source 30a and a phosphor layer 30b. The excitation light source 30a is, for example, a blue LED light source that generates blue light having a center wavelength of approximately 450 nm as excitation light. The phosphor layer 30b is made of a resin material scattered with yellow phosphors, and generates yellow fluorescence upon receipt of the excitation light from the excitation light source 30a. As an example of the yellow phosphors, YAG ($Y_3Al_5O_{12}$) phosphors are employed.

Figure 3A:
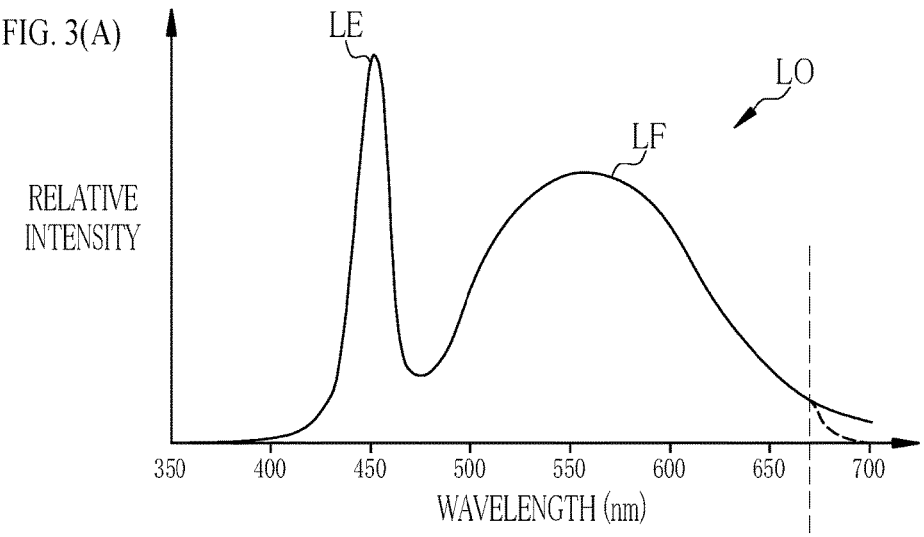
FIG. 3(A) is a graph showing an intensity spectrum of output light emitted from a white LED light source.

Part of components of the excitation light generated by the excitation light source 30a passes through the phosphor layer 30b without being converted to the fluorescence in the phosphor layer 30b. Thus, as shown in FIG. 3(A), the white LED light source 30 emits light (hereinafter referred to as output light LO) that is a mixture of the fluorescence LF and the excitation light LE.

The excitation light LE is blue light and the fluorescence LF is yellow light. Thus, the output light LO has an intensity spectrum continuous across blue, green and red regions. The output light LO has a wavelength band ranging approximately from 400 to 750 nm. This output light LO enters the band limiting section 32. Note that the output light LO preferably includes wavelength components of not lower than 700 nm.

Figure 3B:
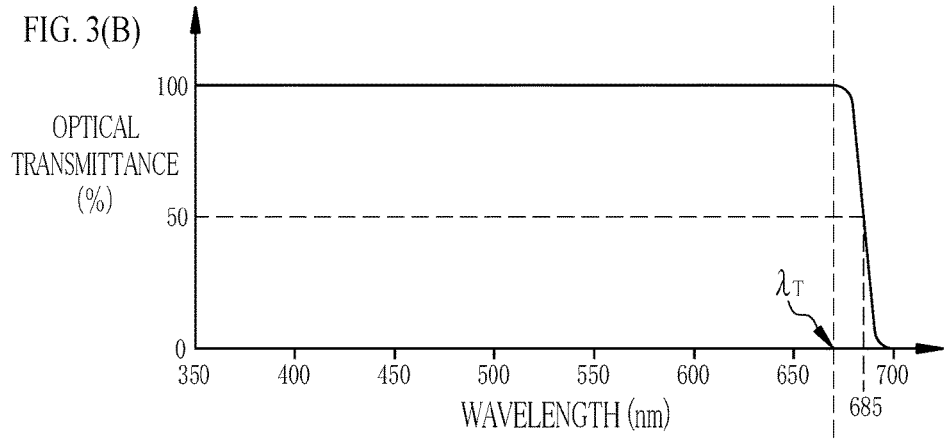
FIG. 3(B) is a graph showing light transmission characteristics of a band limiting section.

As shown in FIG. 3(B), the band limiting section 32 is a narrow band filter having such light transmission characteristics that reduce light in a wavelength band of not lower than a threshold $\lambda_T$. In the present embodiment, $\lambda_T$=670 nm. The optical transmittance of the band limiting section 32 is substantially 100% in a wavelength band of lower than approximately 670 nm, and substantially 0% in a wavelength band of not lower than approximately 700 nm. The half-power point wavelength of the band limiting section 32 is approximately 685 nm. As shown in FIG. 3(A), the band limiting section 32 reduces the light intensity of the output light LO in a wavelength band of not lower than approximately 670 nm.

After transmitted through the band limiting section 32, the output light LO enters as illumination light through a condenser lens 33 into the light guide 34. The light guide 34 is built in the endoscope 12 and the universal cord 25, and conducts the illumination light from the light source unit 14 to the tip portion 12d of the endoscope 12. Note that multi-mode optical fibers may serve as the light guide 34. As an example, a fine fiber cable having a core diameter of approximately 105 μm, a cladding diameter of approximately 125 μm, and an external diameter of 0.3 to 0.5 mm inclusive of a cable jacket (protection layer).

In the tip portion 12d of the endoscope 12 are provided lighting optics 35a and imaging optics 35b. The lighting optics 35a has a lighting lens 36. The illumination light from the light guide 34 is projected through the lighting lens 36 to the observation object. Note that the "illuminating section" in the present invention corresponds to a feature including the light guide 34 and the lighting lens 36.

The imaging optics 35b has an objective lens 37, a zooming lens 38 and an imaging device 39. Light components of the illumination light which are returned from the observation object fall on the imaging device 39 through the objective lens 37 and the zooming lens 38. Thus, an optical image of the observation object is formed on the imaging device 39.

The zooming lens 38 moves between a telephoto terminal and a wide-angle terminal according to the operation on the zooming section 13. The zooming lens 38 is located at the wide-angle terminal when no close-up observation is made (during non-close-up observation). To make a close-up observation, the zooming lens 38 is moved from the wide-angle terminal to the telephoto terminal according to the operation on the zooming section 13.

The imaging device 39 is a synchronous primary color sensor which captures the optical image of the observation object and outputs color image signals. As the imaging device 39, a CMOS (complementary metal-oxide semiconductor) image sensor is adopted.

Figure 4:
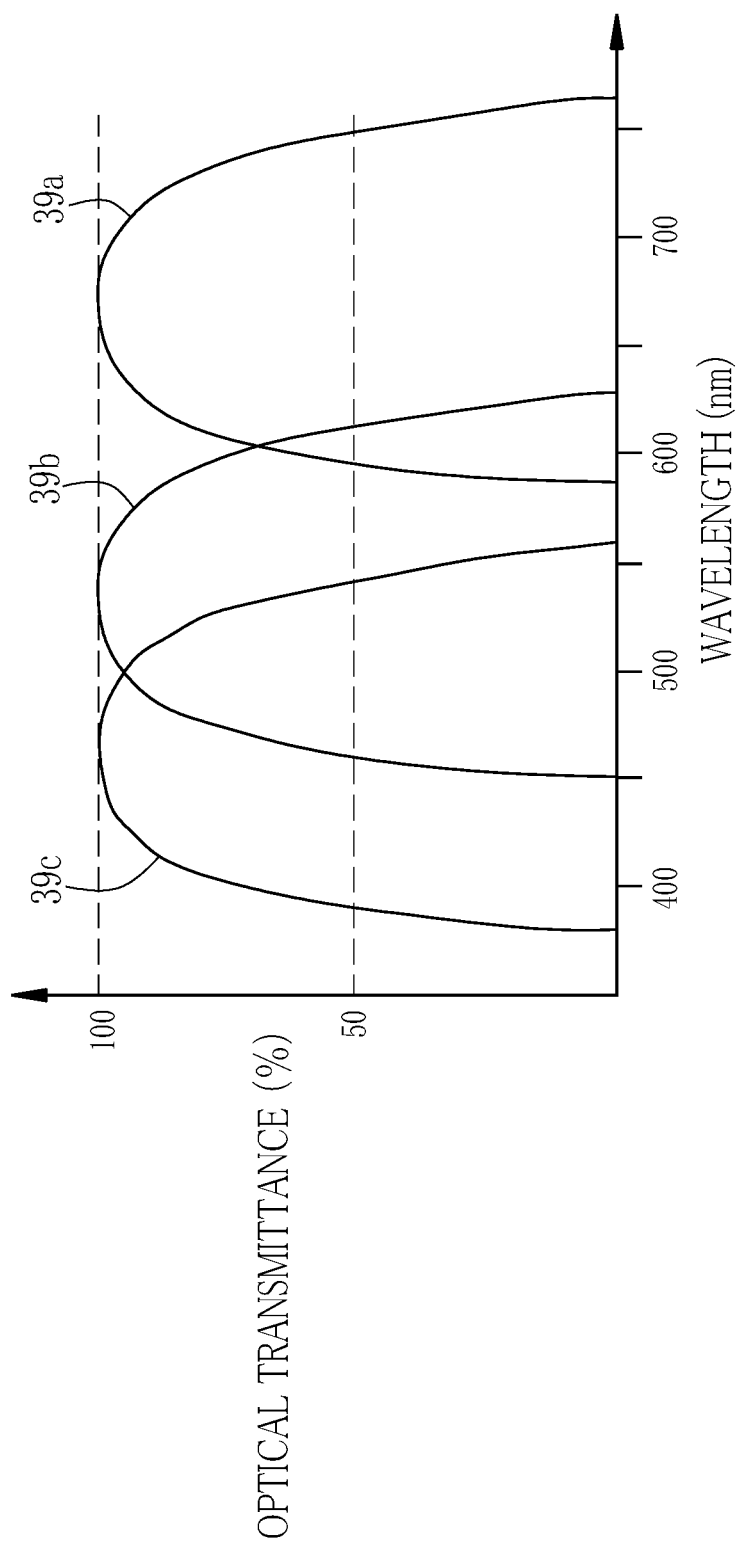
FIG. 4 is a graph showing spectral characteristics of color filters.

Referring to FIG. 4, the imaging device 39 includes red (R) color filters having first spectral transmission characteristics 39a, green (G) color filters having second spectral transmission characteristics 39b and blue (B) color filters having third spectral transmission characteristics 39c. Each pixel of the imaging device 39 is provided with any one of the color filters. That is, the imaging device 39 has R pixels with the R color filters, G pixels with the G color filters and B pixels with the B color filters, thereby outputting RGB image signals. The RGB image signals consist of red image signals, green image signals and blue image signals, wherein one color signal of red, green or blue is assigned to one pixel.

The imaging device 39 is provided with a correlated double sampling circuit and an A/D (analog-to-digital) converter, and outputs the image signals as digital signals.

The processor unit 16 is provided with an imaging controller 40, a signal receiver 41, a DSP (digital signal processor) 42, a noise reducer 43, an observation image producer 44 and a video signal producer 45. The imaging controller 40 controls the imaging timing of the observation object by the imaging device 39 and the output timing of the color image signals from the imaging device 39.

The signal receiver 41 receives the digital RGB image signals output from the imaging device 39 of the endoscope 12. The DSP 42 renders the received RGB image signals with various kinds of signal processing, such as defect correction, offsetting, gain correction, linear matrix processing, gamma conversion and demosaicing.

The defect correction process is to correct signals from defective pixels of the imaging device 39. In the offsetting process, dark current components are eliminated from the RGB image signals, which have undergone through the defect correction process, to set up the exact zero level. In the gain correction process, the RGB image signals after the offsetting process is multiplied by a particular gain value to regulate the signal level. After the gain correction process, the RGB image signals are rendered with a linear matrix process for improving the color reproduction. Thereafter, a gamma conversion process is applied to control the luminance and the color saturation. After the linear matrix processing, the RGB image signals are subjected to a demosaicing process (also called synchronizing process) to produce red, green and blue color signals with respect to each pixel.

The noise reducer 43 reduces noises by treating the RGB image signals under gone through the demosaicing and other processes in DSP 42 with a noise reduction process (a process including mean filtering, medial filtering or the like). After the noise reduction, the RGB image signal is fed to the observation image producer 44.

The observation image producer 44 processes the RGB image signals from the noise reducer 43 for image rendering, such as color conversion, color enhancement and structure enhancement, to produce an observation image. The color conversion of the RGB image signals is performed mainly by 3-by-3 matrix processing, gradation conversion and 3D LUT (lookup table) process. The color enhancement is performed on the RGB image signal after the color conversion. The structure enhancement is a process for enhancing the structure of the observation object, such as superficial blood vessels and pit patterns, and is performed on the RGB image signals after the color enhancement.

The observation image produced by the observation image producer 44 is input to the video signal producer 45. The video signal producer 45 converts the observation image to a video signal for displaying the image on the monitor 18. The monitor 18 displays an image on the basis of the video signal from the video signal producer 45.

Figure 3C:
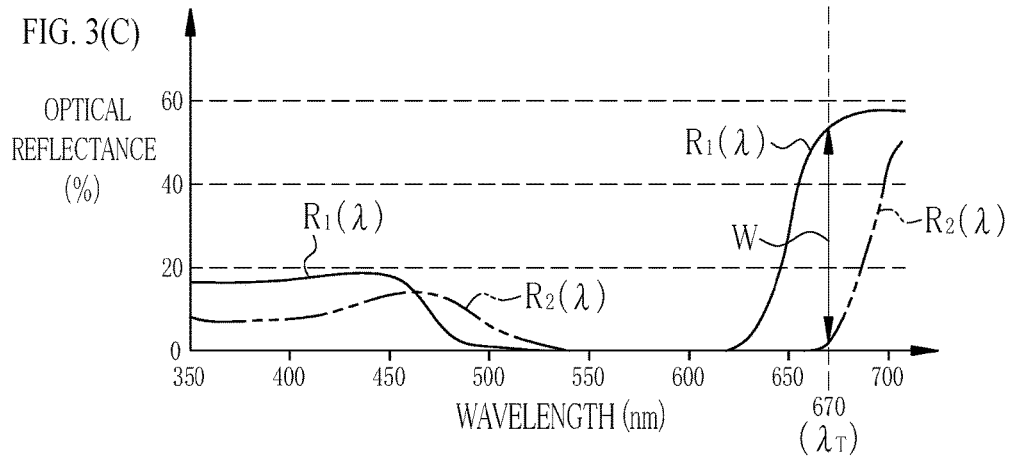
FIG. 3(C) is a graph showing light reflection characteristics of pyoktanin and indigocarmine.

FIG. 3(C) shows an optical reflection characteristic curve $R_1(\lambda)$ of pyoktanin and an optical reflection characteristic curve $R_2(\lambda)$ of indigocarmine, which may be sprayed on the observation object. The optical reflectance of pyoktanin is above a certain level in a wavelength band of not higher than approximately 470 nm and in a wavelength band of not lower than approximately 640 nm. The optical reflectance of indigocarmine is above a certain level in a wavelength band of not higher than approximately 520 nm and in a wavelength band of not lower than approximately 670 nm.

At the threshold $\lambda_T$ of the band limiting section 32, the optical reflectance of pyoktanin is equal to or more than a constant value Rc, whereas the optical reflectance of indigocarmine is nearly zero. Thus, the threshold $\lambda_T$ satisfies relations: $R_1(\lambda_T) \geq Rc$ and $R_2(\lambda_T) \approx 0$. In the present embodiment, $\lambda_T = 670$ nm and the constant value Rc is a value within a range W of 5-55% shown in FIG. 3(C), e.g. Rc=40%. Moreover, the relation "$R_2(\lambda_T) \approx 0$" means that the optical reflectance is substantially zero and excluded from the range W, satisfying a relation: $R_2(\lambda_T) < 5\%$.

As shown by a broken line in FIG. 3(A), since the intensity of the illumination light is reduced in a wavelength band of not lower than the threshold $\lambda_T$ (=670 nm) by the band limiting section 32, light reflected from indigocarmine substantially contains only wavelength components of not higher than approximately 520 nm. Whereas light reflected from pyoktanin contains wavelength components of approximately from 640 to 670 nm in addition to wavelength components of not higher than approximately 470 nm.

Therefore, in the observation image displayed on the monitor 18, portions stained with pyoktanin will appear in violet, and portions stained with indigocarmine will appear in blue. Thus, the difference in color between pyoktanin (the first dye) and indigocarmine (the second dye) is clarified in the observation image.

Now the operation of the endoscopy system 10 according to the present embodiment will be described. First, a user like a doctor makes a distant view observation and screening on a test body, such as a large intestine, while inserting the insertion section 12a of the endoscope 12 into the test body. For this purpose, a light emitting operation by the light source unit 14, an imaging operation by the imaging device 39 in the endoscope 12, an observation image producing operation by the processor unit 16, and an image displaying operation for displaying the observation image on the monitor 18 are carried out.

In the light source unit 14, the light source controller 31 drives the excitation light source 30a in the white LED light source 30 to emit the blue excitation light LE, and the phosphor layer 30b as receiving the excitation light LE generates yellow fluorescence LF. Thus, the white LED light source 30 emits the output light LO as a mixture of the fluorescence LF and partial components of the excitation light LE. The output light LO enters the band limiting section 32, and the band limiting section 32 reduces the light intensity in a wavelength band of not lower than approximately 670 nm.

The output light LO transmitted through the band limiting section 32 is formed into the illumination light through the condenser lens 33 and enters the light guide 34. The illumination light entering the light guide 34 is projected from the tip portion 12d of the endoscope 12, thereby illuminating the observation object.

The observation object illuminated with the illumination light is imaged by the imaging device 39 in the endoscope 12. The imaging device 39 produces digital RGB image signals and inputs ones to the processor unit 16. In the processor unit 16, the DSP 42 renders the RGB image signals with various kinds of signal processing, and the noise reducer 43 reduces the noises. Then, the RGB image signals are input to the observation image producer 44, which subjects the input image signals to various kinds of image processing to produce an observation image. The observation image is displayed on the monitor 18 through the video signal producer 45. The displayed observation image seems reddish because hemoglobin in the observation object absorbs short wavelength rays.

If the user detects any site that may be a lesion, the site (the suspected lesion) being brownish, reddened or the like, during the screening, the user operates the zooming section 13 to make a close-up observation by enlarging an area of the observation object, including the suspected lesion. In addition, the user makes dye-spraying to the observation object in order to make the suspected lesion more visible. Specifically, the user operates the injection syringe 24, which is filled with a dye such as pyoktanin or indigocarmine, to spray the dye from the distal end 22a of the spray tube 22 onto the observation object while checking the position of the distal end 22a in the enlarged observation image.

In the close-up observation, the light emitting operation, the imaging operation, the observation image producing operation and the image displaying operation are carried out in the same way as in the distant view observation. Thus, the monitor 18 displays an observation image including the suspected lesion stained with the dye.

As described above, the illumination light has a reduced light intensity in the wavelength band of not lower than approximately 670 nm in the present embodiment. Therefore, in the observation image on the monitor 18, the area stained with pyoktanin is perceived as a violet area and the area stained with indigocarmine is perceived as a blue area.

Thus, when inspected through the endoscopy system 10 of the present embodiment, the observation object exhibits a clear difference in color between a case where pyoktanin has been sprayed thereon and a case where indigocarmine has been sprayed thereon. Therefore, the user like a doctor is enabled to determine the symptom of a lesion more precisely.

Although the threshold $\lambda_T$ of the band limiting section 32 is set at 670 nm in the above embodiment, the threshold $\lambda_T$ is not limited to 670 nm but may be any value that satisfies the relations: $R_1(\lambda_T) \geq Rc$ and $R_2(\lambda_T) \approx 0$. Furthermore, the half-power point wavelength of the band limiting section 32 is not limited to 685 nm, but may be preferably set according to the threshold $\lambda_T$.

In the above embodiment, the band limiting section 32 is provided in the light source unit 14. However, another band limiting section may be provided in the endoscope 12 in addition to the band limiting section 32 in the light source unit 14. Alternatively, the band limiting section 32 may be provided only in the endoscope 12.

Figure 5:
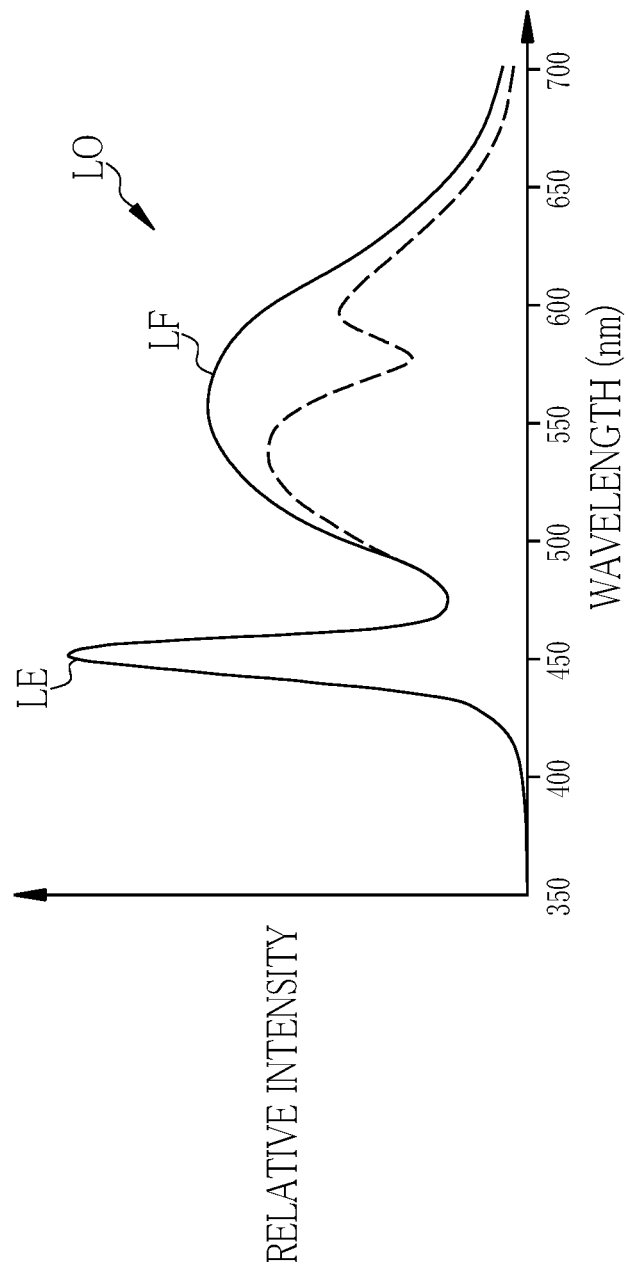
FIG. 5 is a graph showing an intensity spectrum of the output light after being partly intensity-attenuated by a band attenuation filter.
Figure 6:
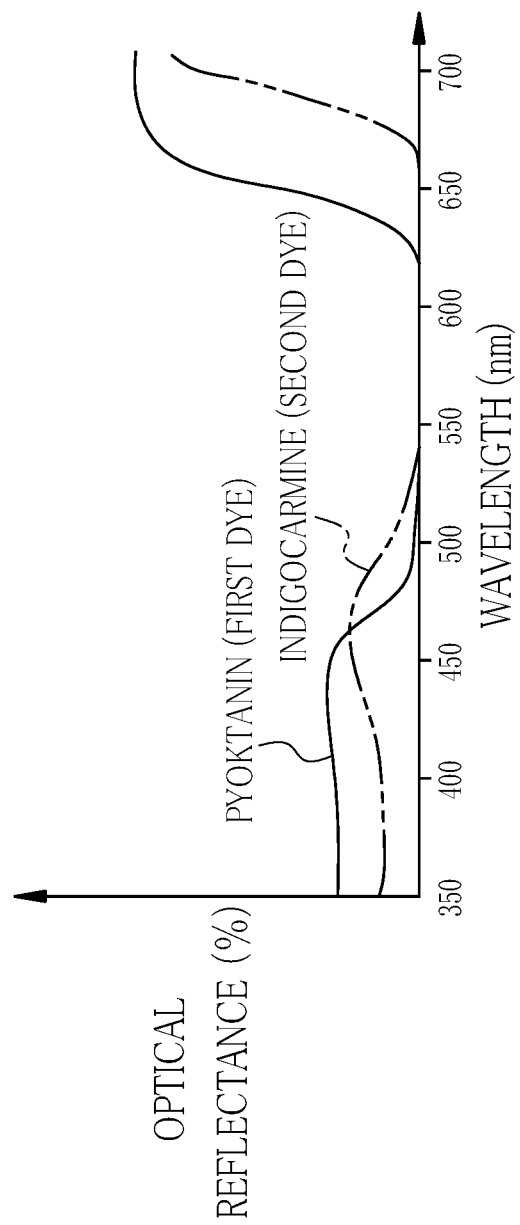
FIG. 6 is a graph showing light reflection characteristics of pyoktanin and indigocarmine.

In the above embodiment, the band limiting section 32 is a narrow band filter that reduces the light intensity in the infrared region. It is also preferable to provide a band attenuation filter that attenuates the light intensity of the output light LO in a wavelength band between the green and red regions, i.e., in a band around 580 nm. Thus, the light intensity of the output light LO is partly reduced as shown by a broken line in FIG. 5, thereby improving color differentiation in the observation image.

The above embodiment specifies that the phosphor layer 30b of the white LED light source 30 is formed by scattering yellow phosphors over the resin material, but the kind of phosphors scattered over the resin material is not limited to the yellow phosphors. For example, the phosphor layer 30b may be a resin material scattered with green phosphors and red phosphors. In that example, $\beta$-SiAlON ($\beta$-Si$_{6-x}$Al$_x$O$_x$N$_{8-}$ x) phosphors may be employed as the green phosphors, and CASN (CaAlSiN$_3$: Eu$^{2+}$) phosphor may be employed as the red phosphors.

Although the excitation light source 30a emits blue excitation light in the above embodiment, the excitation light source may emit excitation light of which the center wavelength is outside the blue region. For example, as the excitation light source 30a, it is possible to use a violet LED that emits excitation light with a center wavelength of approximately 405 nm. In this example, a resin material scattered with blue phosphors, green phosphors and red phosphors may serve as the phosphor layer 30b. BAM (BaMgAl$_{10}$O$_{17}$: Eu$^{2+}$) phosphors are usable as the blue phosphors. β-SiAlON ((β-Si$_{6-x}$Al$_x$O$_x$N$_{8-x}$) phosphors are usable as the green phosphors. CASN (CaAlSiN$_3$: Eu$^{2+}$) phosphors are usable as the red phosphors.

Furthermore, a primary color sensor is used as the imaging device 39 in the above embodiment, but a complementary color sensor may be employed as an alternative. As the complementary color sensor, one having cyan (C) pixels, magenta (Mg) pixels, yellow (Y) pixels and green (G) pixels is preferable. In the example wherein the imaging device 39 is a complementary color sensor, the processor unit 16 should execute an arithmetic operation for converting complementary color image signals (CMYG image signals) to primary color image signals (RGB image signals).

Moreover, the above embodiment uses a CMOS image sensor as the imaging device 39, but a CCD (Charge-Coupled Device) image sensor may be employed as an alternative.

In the above embodiment, the light source unit and the processor unit are configured as separate bodies, but the light source unit and the processor unit may be configured as an integrated device.

The present invention is not to be limited by the above embodiments but may be modified, as appropriate, without departing from the subject matter of the present invention, for example, by combining any of the above embodiments and modifications.

What is claimed is:

1. An endoscopy system which illuminates an observation object stained with a first dye or a second dye having different optical reflection characteristics in a red region from the first dye, comprising:
    a semiconductor illuminant having an excitation light source that generates excitation light and a phosphor layer that is caused by the excitation light to generate fluorescence, the semiconductor illuminant emitting output light that has an intensity spectrum across blue, green and red regions and wavelength components of not lower than 700 nm; and
    a band limiting section that reduces the light intensity of the output light in a wavelength band equal to and higher than a threshold which is not less than 650 nm and at which threshold the first dye on the observation object has an optical reflectance of not less than a constant value and the second dye on the observation object has an optical reflectance of substantially zero;
    an illuminating section that projects illumination light as light transmitted through the band limiting section toward the observation object;
    an imaging device that captures light returned from the observation object and outputs color image signals;
    an observation image producer that produces an observation image by processing the color image signals; and
    a dye spraying section for spraying the first dye or the second dye onto the observation object,
    wherein the first dye has an optical reflectance above a certain level in a wavelength band in the blue region and in a wavelength band lower than the threshold in the red region,
    wherein the second dye has an optical reflectance above a certain level in a wavelength band in the blue region and in a wavelength band not lower than the threshold in the red region,
    wherein the first dye will appear in violet in the observation image, and
    wherein the second dye will appear in blue in the observation image.

2. The light source unit as set forth in claim 1, wherein the intensity spectrum of the output light is continuous across the blue, green and red regions, and the output light includes wavelength components of not lower than 700 nm.

3. The light source unit as set forth in claim 2, wherein the threshold is 670 nm.

4. The light source unit as set forth in claim 1, wherein the first dye is pyoktanin, and the second dye is indigocarmine.

5. The light source unit as set forth in claim 1, wherein the excitation light is blue light having a center wavelength of 450 nm, and the fluorescence is yellow light.

6. The light source unit as set forth in claim 1, wherein the output light is a mixture of the fluorescence and those components of the excitation light which travel through the phosphor layer.

7. The light source unit as set forth in claim 6, wherein the semiconductor illuminant is a white light emitting diode.

* * * * *